(12) United States Patent
Takeuchi

(10) Patent No.: US 8,142,734 B2
(45) Date of Patent: Mar. 27, 2012

(54) MICROPLATE

(75) Inventor: Tomohiko Takeuchi, Shizuoka (JP)

(73) Assignee: Beckman Coulter, Inc., Brea, CA (US)

( * ) Notice: Subject to any disclaimer, the term of this patent is extended or adjusted under 35 U.S.C. 154(b) by 509 days.

(21) Appl. No.: 12/272,160

(22) Filed: Nov. 17, 2008

(65) Prior Publication Data

US 2009/0068067 A1 Mar. 12, 2009

Related U.S. Application Data

(63) Continuation of application No. PCT/JP2007/060158, filed on May 17, 2007.

(30) Foreign Application Priority Data

May 17, 2006 (JP) ................................ 2006-137726

(51) Int. Cl.
*G01N 21/75* (2006.01)
(52) U.S. Cl. ....................................................... 422/407
(58) Field of Classification Search .................... 422/407
See application file for complete search history.

(56) References Cited

U.S. PATENT DOCUMENTS

| | | | | |
|---|---|---|---|---|
| 4,794,450 | A | * | 12/1988 | Saito et al. ........................ 348/61 |
| 5,116,765 | A | * | 5/1992 | Watanabe et al. .............. 436/165 |
| 6,258,326 | B1 | * | 7/2001 | Modlin .......................... 422/553 |
| 6,542,293 | B2 | | 4/2003 | Yahiro |
| 7,410,617 | B2 | | 8/2008 | Sakamoto |
| 2001/0033414 | A1 | | 10/2001 | Yahiro |
| 2005/0106074 | A1 | | 5/2005 | Sakamoto |

FOREIGN PATENT DOCUMENTS

| | | |
|---|---|---|
| JP | 53-91120 A | 8/1978 |
| JP | 05-273216 | 10/1993 |
| JP | H05-273216 | 10/1993 |
| JP | 2001-296478 | 10/2001 |
| JP | 2001-296478 A | 10/2001 |
| JP | 2002-014035 | 1/2002 |
| JP | 2002-14035 A | 1/2002 |
| JP | 2004-045103 | 2/2004 |
| JP | 2004-45103 A | 2/2004 |
| JP | 2004-150807 A | 5/2004 |
| JP | 2005-61919 | 3/2005 |
| JP | 2005-61919 A | 3/2005 |

OTHER PUBLICATIONS

English Translation of Office Action dated Jun. 3, 2011 for corresponding Japanese Patent Application No. 2006-137726, 4 pages; (original JP Office Action previously cited).
International Search Report, International Application No. PCT/JP2007/060158, mailed Jul. 31, 2007, 4 pages.

\* cited by examiner

*Primary Examiner* — Lore Jarrett
(74) *Attorney, Agent, or Firm* — Kilpatrick Townsend & Stockton LLP

(57) ABSTRACT

A microplate in which a plurality of wells that are reaction vessels, in a substantially concave shape, to analyze components of a specimen are arranged in matrix, includes a first surface that passes through an opening plane of the wells; and a second surface that is directed to an opposite side to the first surface. The microplate also includes a well-identification information indicator that is arranged on the second surface included in a boundary portion between wells next to each other, and that indicates well identification information to identify each of the wells. The boundary portion between the wells next to each other has a thickness substantially equivalent to a depth of the wells.

2 Claims, 5 Drawing Sheets

US 8,142,734 B2

MICROPLATE

CROSS-REFERENCE TO RELATED APPLICATIONS

This application is a continuation of PCT international application Ser. No. PCT/JP2007/060158 filed on May 17, 2007 which designates the United States, incorporated herein by reference, and which claims the benefit of priority from Japanese Patent Application No. 2006-137726, filed on May 17, 2006, incorporated herein by reference.

BACKGROUND OF THE INVENTION

1. Field of the Invention

The present invention relates to a microplate in which a plurality of wells that are reaction vessels to analyze components of a specimen are arranged in matrix.

2. Description of the Related Art

When a specimen such as blood and body fluid is analyzed, a microplate in which a plurality of reaction vessels each called well are arranged in matrix is often used (for example, see Japanese Patent Laid-Open Publication No. H05-273216). In each well of a microplate, a specimen including a substance of an analysis object and a reaction reagent including a substance that causes an antigen-antibody reaction with the substance of the analysis object are dispensed. After a predetermined time from this dispensation, the reaction caused in the well is imaged by an imaging means such as a CCD (charge coupled device) camera, and components of the specimen are analyzed using image data obtained by imaging.

Conventionally, to identify respective wells accurately at such analysis, a microplate with identification information in which identification information such as a well number is provided on a surface near an opening plane of each well has been supplied.

SUMMARY OF THE INVENTION

A microplate according to an aspect of the present invention in which a plurality of wells that are reaction vessels, in a substantially concave shape, to analyze components of a specimen are arranged in matrix, includes a first surface that passes through an opening plane of the wells; a second surface that is directed to an opposite side to the first surface; and a well-identification information indicator that is arranged on the second surface included in a boundary portion between wells next to each other, and that indicates well identification information to identify each of the wells. The boundary portion between the wells next to each other has a thickness substantially equivalent to a depth of the wells.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments (hereinafter, "embodiment") according to the present invention are explained with reference to the accompanying drawings.

Figure 1:
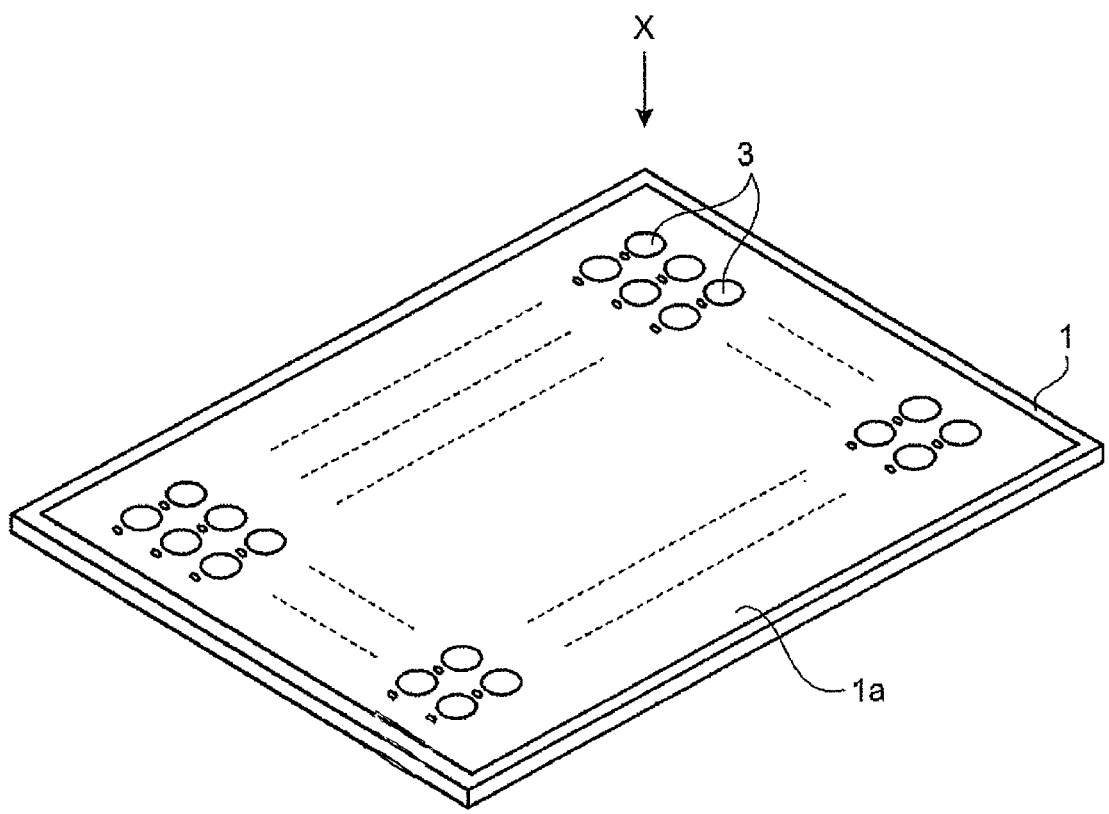
FIG. 1 is a perspective view showing a structure of a microplate according to an embodiment of the present invention.
Figure 2:
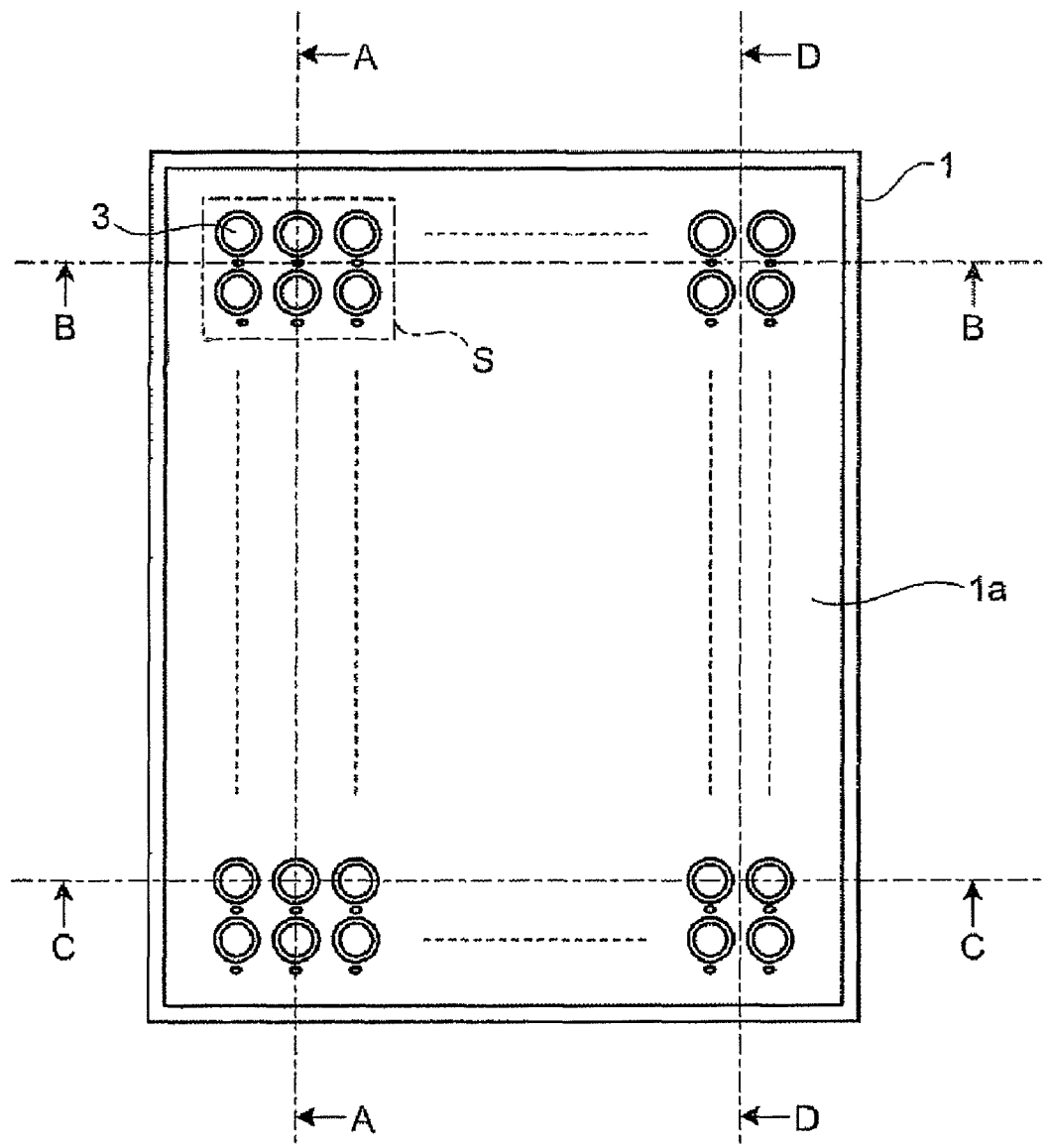
FIG. 2 is a front view showing a structure of the microplate according to the embodiment of the present invention.

FIG. 1 is a perspective view showing a schematic structure of a microplate according to an embodiment of the present invention. Further, FIG. 2 is a front view of the microplate viewed from a direction of arrow X shown in FIG. 1. A microplate 1 shown in these figures has circular openings, and is formed such that a plurality of wells 3 that are reaction vessels in a substantially concave shape in which a specimen and a reagent are dispensed to cause a reaction therein are arranged in matrix. On a surface 1b (second surface) on a rear side that is directed to an opposite side to a surface 1a (first surface) on a front side on an opening plane of the wells 3, well-identification information indicators that indicate well identification information to identify each of the wells 3 are provided at predetermined positions near the corresponding wells 3. This microplate 1 is formed by injection molding synthetic resin such as acrylic.

Figure 3:
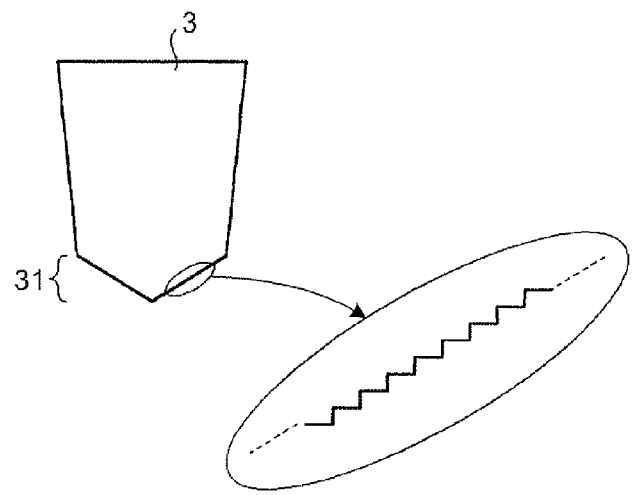
FIG. 3 is an explanatory diagram showing a structure of a well bottom.

Any cross-section (horizontal cross-section) in a direction parallel to the opening plane of the well 3 is circle, and a diameter of the circle on each horizontal cross-section becomes smaller gradually toward a bottom from the opening plane. Particularly, a bottom 31 serving as a liquid containing basin at the time of dispensation is in a substantially circular conic shape. An inclined portion in this bottom 31 has such a configuration that a diameter thereof changes slightly stepwise to increase surface area thereof so that precipitation of a reactant condensed as a result of an antigen-antibody reaction is facilitated. FIG. 3 is an explanatory diagram schematically showing the configuration of the bottom 31 of the well 3 whose diameter on the horizontal cross-section changes stepwise.

Figure 4:
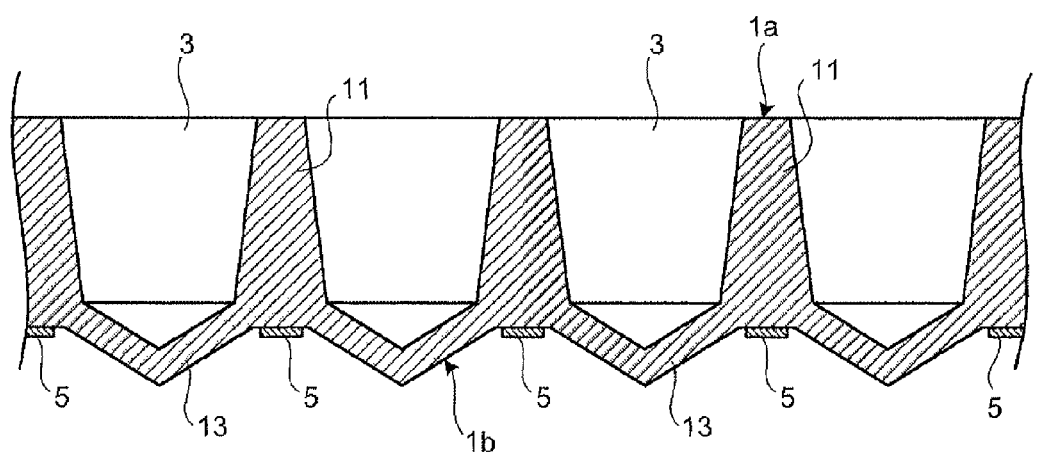
FIG. 4 is an enlarged partial cross-section taken along line A-A shown in FIG. 2.

FIG. 4 is an enlarged partial cross-section showing a part of an area at which the well-identification information indicator 5 is provided, out of the A-A cross-section (vertical cross-section) of FIG. 2 that passes through the deepest point of the well 3. As shown in the vertical cross-section in the figure, the microplate 1 has an upper projection 11 that projects toward an opening side of the well 3 regularly. Furthermore, a bottom surface 13 of the microplate 1 on this cross-section has substantially the same shape as the bottom 31 of the well 3, and the thickness thereof is substantially uniform. A bottom surface of the upper projection 11 on a side of the surface 1b is included in a boundary portion between the wells 3 next to each other, and is arranged substantially parallel to the surface 1a. At the bottom surface on the side of this surface 1b, the well-identification information indicator 5 is arranged by affixing thereon or the like.

As is apparent from FIG. 4, the thickness of the microplate 1 at the boundary portion between the wells 3 next to each other is substantially equal to the depth of the wells 3. Accordingly, the distance from a predetermined position at an upper portion of the microplate 1 to a portion near the bottom 31 of the well 3 and the distance from the same predetermined position to the well-identification information indicator 5 are substantially identical. Therefore, if the bottom 31 of the well 3 is imaged using an imaging means that is arranged above the microplate 1, the bottom 31 can be imaged in a state where the well-identification information indicator 5 is also focused.

All vertical cross-sections that pass through the deepest point of the well 3 parallel to the A-A cross-section have the same shape as that shown in FIG. 4. Moreover, the shapes near the well 3 on C-C cross-section shown in FIG. 2 and a vertical cross-section that passes through the deepest point of the well 3 parallel to the C-C cross-section are the same as the enlarged partial cross-section shown in FIG. 4 except the point that the well-identification information indicator 5 is not attached.

Figure 5:
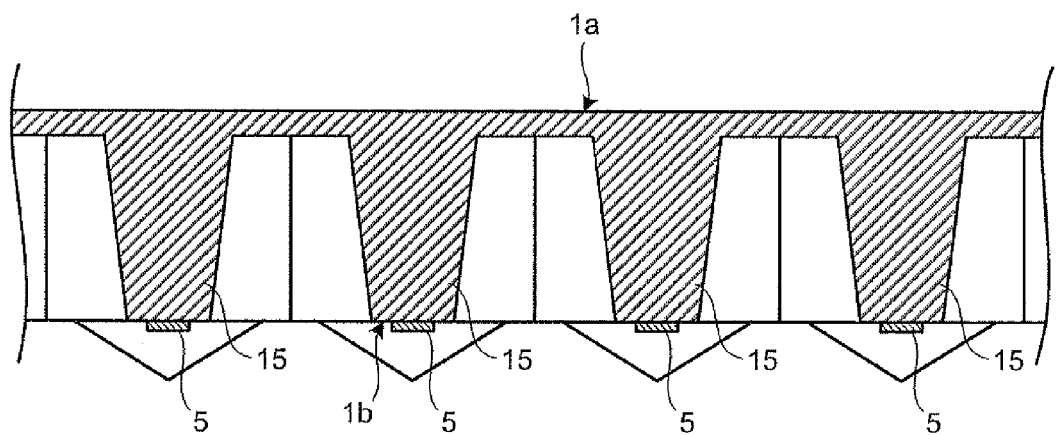
FIG. 5 is an enlarged partial cross-section taken along line B-B shown in FIG. 2.

FIG. 5 is an enlarged partial cross-section showing the boundary portion between the wells 3 next to each other, out of the B-B cross-section shown in FIG. 2, which is the vertical cross-section of the microplate 1 perpendicular to the A-A cross-section described above. On the vertical cross-section shown in the figure, the microplate 1 has a lower projection 15 that projects toward the bottom of the well 3 regularly. The surface 1*b* being an end surface of the lower projection 15 is included in the boundary portion between the wells 3 next to each other, and corresponds to a bottom surface of the above described upper projection 11 that is substantially horizontal. On this surface 1*b*, the well-identification information indicator 5 is provided by affixing thereon, or the like.

All vertical cross-sections that pass through the boundary portion between the wells 3 next to each other parallel to the B-B cross-section have the same shape as that shown in FIG. 5. Moreover, the shapes of D-D cross-section of FIG. 2 and a vertical cross-section that passes through the boundary portion between the wells 3 next to each other parallel to the D-D cross-section are the same as the enlarged partial cross-section shown in FIG. 5 except the point that the well-identification information indicator 5 is not attached.

Figure 6:
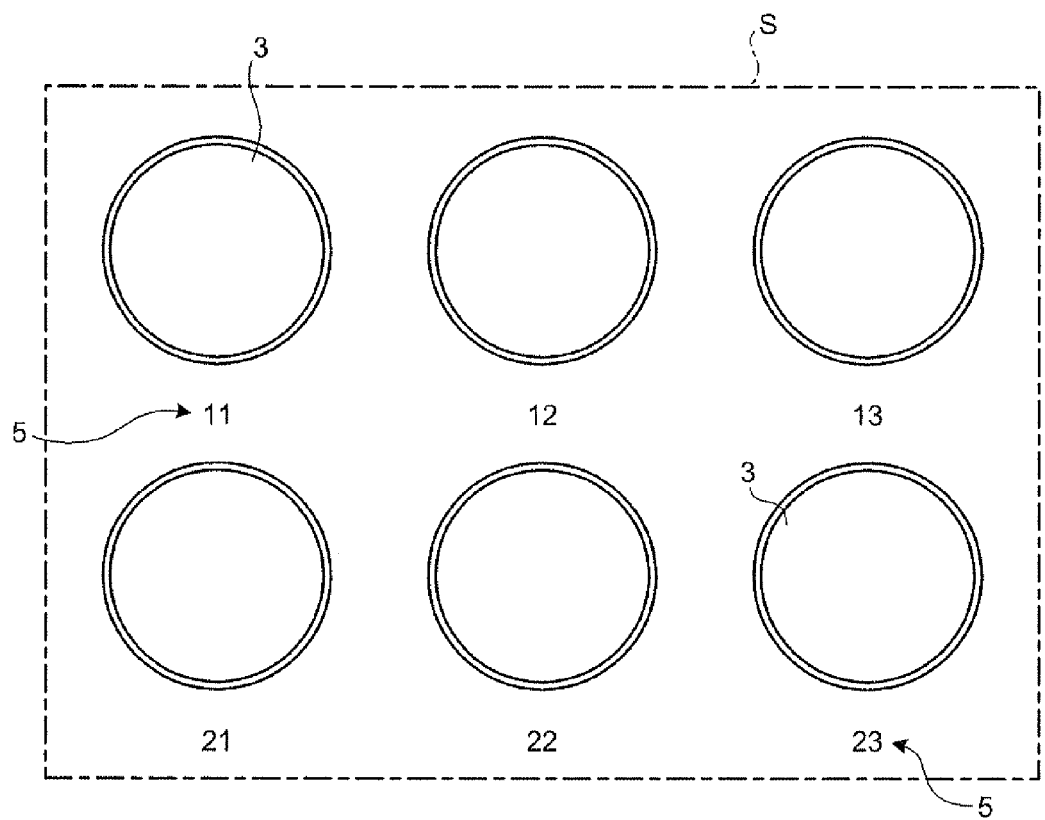
FIG. 6 is an enlarged view of a section S shown in FIG. 2.

FIG. 6 is an enlarged view of section S shown in FIG. 2 illustrating a specific example of forming the well-identification information indicator 5. In the example shown in FIG. 6, a combination of a row number and a column number of each of the wells 3 when the well 3 positioned at an upper left end in the section S is a starting point (that is, first row in first column) of rows and columns is used as the well identification information. Therefore, for example, well identification information indicated as "23" indicates that the well 3 positioned above the well-identification indicator 5 indicating this well identification information in FIG. 6 is positioned in the second row in the third column relative to the well 3 positioned at the upper left end in the section S as the starting point. Also for the other wells 3 not shown in FIG. 6, the combination of the row number and the column number relative to the well 3 at the upper left end in the section S as the starting point is used as the well identification information, and the combination is indicated by the appropriate well-identification information indicator 5 of each. The well identification information can take any form as long as each of the wells 3 can be identified, and symbols or patterns other than numerals, or color can be used to form the well-identification information indicator 5.

In the microplate 1 having the above structure, when a specimen such as blood and body fluid and a reagent including substance that causes a specific reaction with a certain substance in the specimen are respectively dispensed for an appropriate amount in the wells 3, the substances causes an antigen-antibody reaction inside the wells 3. For example, when blood typing is performed using red corpuscles in blood, the red corpuscles causes an antigen-antibody reaction with a certain antigen included in a reagent to be condensed. The condensed red corpuscles precipitate at the inclined portion in steps of the bottom 31. The condensation pattern formed by the precipitation differs depending on a blood type, and therefore, by analyzing image data that is obtained by imaging the condensation pattern by an appropriate imaging means, the blood type of the specimen is determined. Because the condensation pattern obtained by the antigen-antibody reaction appears at the inclination portion of the bottom 31 of the well 3, to image this condensation pattern, it is required to take the focus position of the imaging means near the bottom 31.

In the microplate 1 according to the embodiment, the well-identification information indicator 5 is attached on the surface 1*b* having distance, from the opening plane, substantially equivalent to the depth from the opening plane of the well 3 to the deepest point of the bottom 31, and therefore, the distance from the imaging means to the bottom 31 and the distance from the imaging means to the well-identification information indicator 5 are substantially the same. Accordingly, if the condensation pattern near the bottom 31 is imaged, the well-identification information indicator 5 near the well 3 is also focused, and therefore, image data necessary for the analysis can be obtained by single imaging. As a result, a fixed focus camera not requiring a mechanism to control a focus position becomes applicable as the imaging means, and the control at the time of imaging a reaction pattern can be executed easily without much time and work, and the cost for the imaging means can be low.

According to the microplate of the embodiment of the present invention explained above, the distance from an imaging means to a portion near the bottom of a well and the distance from the imaging means to the well identification information can be made substantially the same. Therefore, imaging of a condensation pattern caused as a result of reaction of a specimen and a reagent and well identification information can be done at the same time, and image data necessary for analysis of the specimen can be accurately obtained by single imaging. As a result, an expensive camera is not required, the control becomes simple, time and work required to accurately obtain data necessary for the analysis of a specimen are less, and cost required for the analysis can be low.

Furthermore, according to the embodiment, image data can be generated by single imaging as described above, and therefore, credibility of the image data itself is increased, and the image data can be used as a legal evidence as necessary.

Figure 7:
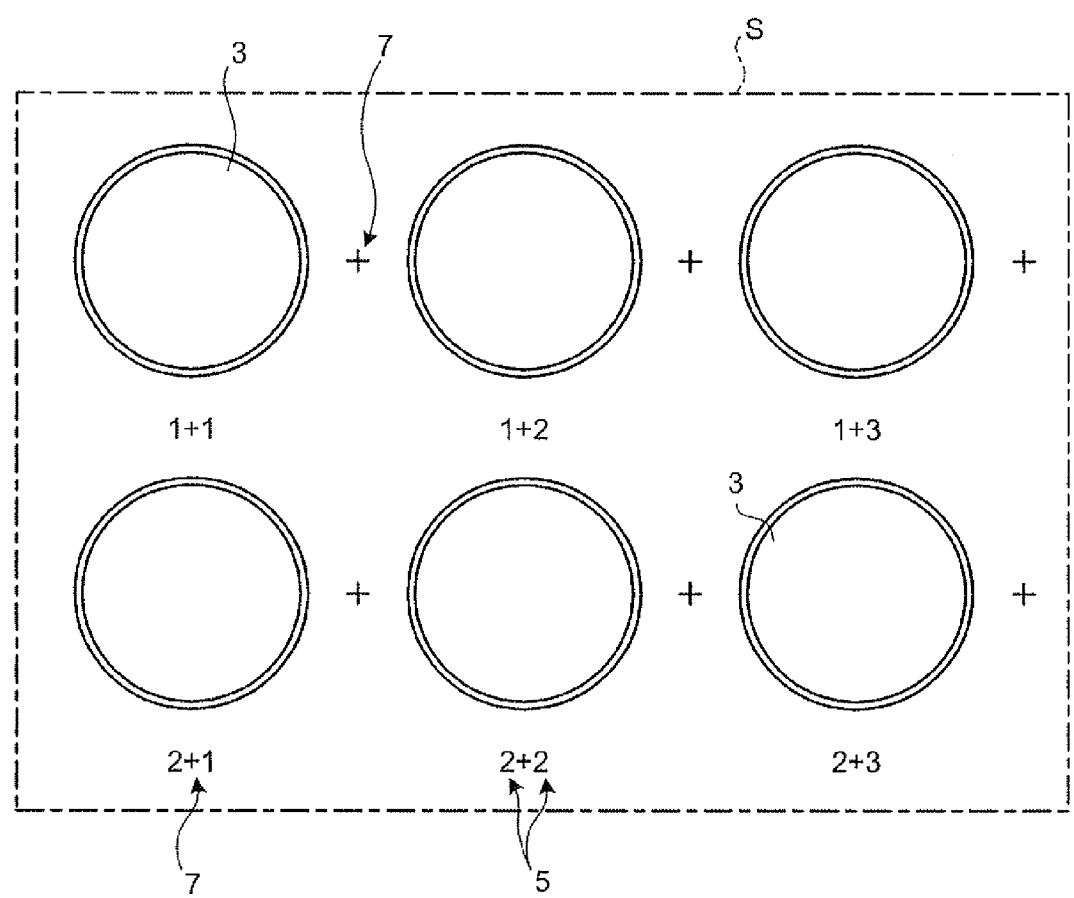
FIG. 7 is a front enlarged view showing a structure of a microplate according to a modification of the embodiment of the present invention.

FIG. 7 is a partial enlarged view of a surface of a microplate according to a modification of the embodiment of the present invention. The section S shown in this figure corresponds to the section S shown in FIG. 2. The feature of the modification is that a center-position determining marker 7 to determine a central position of each of the wells 3 accurately is additionally provided on the surface 1*b* included in the boundary portion between the wells 3 next to each other.

In the example shown in FIG. 7, the center-position determining marker 7 of the well 3 indicated by "+" is provided by affixing from a rear surface to the boundary portion between the wells 3 next to each other in the horizontal direction. In this case, the central position (corresponding to the lowest point) of the well 3 is positioned at intersection of an extended line of a straight line constituting the center-position determining marker 7 closest to the well 3 and an extended line of another center-position determining marker 7. Therefore, at the boundary portion of the wells 3 at which the well-identification information indicator 5 is attached in the above embodiment, the center of a symbol "+" is arranged at the midpoint between the central positions of the wells 3 next to each other, and a row number and a column number are arranged on the left side and the right side of the center-position determining marker 7, respectively, thereby forming the well-identification information indicator 5. Accordingly, for example, the well-identification information indicator 5 and the center-position determining marker 7 for the well 3 in the second row in the third column are formed to indicate "2+3".

Out of the well-identification information indicator 5 and the center-position determining marker 7, the one accuracy of the position is required is the center-position determining marker 7. Therefore, as long as the position of the center-position determining marker 7 is accurate, the well-identification information indicator 5 can take any form as long as the well-identification information indicator 5 is formed such that each of the wells 3 is identifiable and has the size attachable on the bottom surface of the upper projection 11 and the end surface of the lower projection 15.

According to the modification of the embodiment of the present invention, by providing the center-position determining marker in addition to the well-identification information indicator, determination of the central position of each of the wells in image data is further facilitated, and analysis time can be further reduced.

The exemplary embodiment of the present invention has been described in detail, but the present invention is not limited to this embodiment. For example, if a microplate-identification information indicator that indicates microplate identification information to identify a microplate itself is additionally attached at a predetermined position on a rear surface of a peripheral portion of a surface of the microplate, it is possible to identify the microplate also by single imaging.

Furthermore, taking advantage of a configuration with projections and depressions on the rear surface of the microplate according to the present invention as described above, if a thermal plate that can be engaged with this configuration on the rear surface is used so that heat is conducted uniformly to the respective wells to reduce temperature differences between the wells, it becomes possible to perform analysis works further effectively and accurately.

Thus, the present invention can include various embodiments not described herein, and various design modifications and the like can be done within a scope without departing from the technical idea specified by claims.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A microplate in which a plurality of wells that are reaction vessels, in a substantially concave shape, to analyze components of a specimen are arranged in a matrix, the microplate comprising:
    a first surface comprising first portions of an opening plane of the wells different from second portions of the opening plane which are openings of the wells;
    a second surface that is directed to an opposite side to the first surface; and
    a well-identification information indicator that is arranged on the second surface included in a boundary portion between wells next to each other such that the well-identification information indicator is opposite one of said first portions, and that indicates well identification information to identify each of the wells, wherein
    a distance from said second surface in the boundary portion of the wells where the well-identification information indicator is arranged to the first surface is substantially identical to a depth of the wells which is a distance from the bottom of wells to said first surface.

2. The microplate according to claim 1, further comprising a center-position determining marker to determine a central position of a well near the boundary portion, the center-position determining marker arranged on the second surface included in the boundary portion of the wells next to each other.

* * * * *